(12) United States Patent
Forsyth

(10) Patent No.: US 7,913,570 B2
(45) Date of Patent: Mar. 29, 2011

(54) ENVIRONMENTAL DAMAGE SENSOR

(75) Inventor: David Sean Forsyth, Austin, TX (US)

(73) Assignee: Texas Research International, Inc.

( * ) Notice: Subject to any disclaimer, the term of this patent is extended or adjusted under 35 U.S.C. 154(b) by 397 days.

(21) Appl. No.: 12/074,915

(22) Filed: Mar. 8, 2008

(65) Prior Publication Data

US 2009/0223833 A1   Sep. 10, 2009

(51) Int. Cl.
*G01B 7/16*   (2006.01)
(52) U.S. Cl. ............................ 73/779; 73/862.69; 73/808
(58) Field of Classification Search .................... 73/760, 73/779, 808, 862.69
See application file for complete search history.

(56) References Cited

U.S. PATENT DOCUMENTS

| | | | |
|---|---|---|---|
| 4,019,133 | A | 4/1977 | Manley et al. |
| 4,238,298 | A | 12/1980 | Tsuru et al. |
| 4,806,849 | A | 2/1989 | Kihara et al. |
| 4,857,842 | A | 8/1989 | Sturman et al. |
| 5,336,998 | A | 8/1994 | Watts et al. |
| 5,446,369 | A | 8/1995 | Byrne et al. |
| 5,793,279 | A | 8/1998 | Nepela |
| 5,859,537 | A | 1/1999 | Davis et al. |
| 6,054,038 | A | 4/2000 | Davis et al. |
| 6,328,878 | B1 | 12/2001 | Davis et al. |
| 6,628,111 | B2 | 9/2003 | Shapiro et al. |
| 6,828,897 | B1 | 12/2004 | Nepela |
| 6,843,135 | B2 * | 1/2005 | Douglas et al. ................. 73/799 |
| 6,927,948 | B2 | 8/2005 | Gill |
| 6,952,095 | B1 * | 10/2005 | Goldfine et al. .............. 324/240 |
| 7,106,055 | B2 | 9/2006 | Goldfine et al. |

\* cited by examiner

*Primary Examiner* — Max Noori
(74) *Attorney, Agent, or Firm* — M.A. Ervin & Associates; Michael A. Ervin

(57) ABSTRACT

A sensor apparatus for measuring environmental degradation of a structures making use of exposed sacrificial material coupons mounted in the immediate vicinity of magnetic sensor elements in the environment of the monitored structure.

8 Claims, 3 Drawing Sheets

ENVIRONMENTAL DAMAGE SENSOR

TECHNICAL FIELD

This invention relates to the general field of sensors and more specifically to sensors for measuring damaging environmental conditions of structures such as corrosion, coatings breakdowns, and fatigue.

BACKGROUND

A major goal in environmental testing has long been to create a sensor that could be utilized in field or service conditions to detect corrosion and adhesion on metal structures of any size before significant degradation has occurred.

One example is the aging fleets of aircraft in use both in the military and commercial sectors, where corrosion of body and support component surfaces in secluded areas is of crucial concern. Current efforts to detect corrosion on aircraft surfaces consist of visual inspection of the accessible surfaces on a routine basis. Aircraft surfaces that are difficult to access often receive less attention and may not be inspected until aircraft overhaul, which typically occurs every five years. The overhaul process involves the disassembly of the body of the aircraft. The body panels are removed and inspected leaving only a frame skeleton. This process has often revealed corrosion problems in many of the remote areas of the dismantled aircraft. Potential safety concerns prompt the need for continuous corrosion detection capabilities in secluded aircraft compartments.

Evaluation of materials and coatings and the determination or prediction of corrosion performance of both painted and uncoated metal structures or specimens under ambient field or service conditions has traditionally involved visual comparisons which are subjective and require blistering, rusting, or other advanced stages of degradation. The use of laboratory techniques, such as electrochemical impedance spectroscopy (EIS- or AC impedance) has been used to understand and predict corrosion performance during immersion exposures in different electrolytes was limited to small structures or witness specimens that could be immersed, small sections of material cut from large structures, or attachment to the structure of a clamp-on liquid cell in which a liquid or semi-liquid electrolyte and remote counter and reference electrodes were contained.

The immersion of small specimens requires either the destructive sampling of a large structure or the use of witness specimens prepared differently than the actual structure of interest (although the witness specimens and the structure may be prepared at the same time, inherent differences in coating small and large surfaces and inadvertent differences caused by operator error will prevent the witness specimens from being exactly the same as the structure). Additionally, witness specimens will be exposed to slightly different environmental conditions compared to a large structure. Furthermore, the immersion in an electrolyte is not necessarily the exposure condition relevant to the structure being inspected.

Inspection of a large structure using conventional EIS methodologies required complete immersion or use of a clamp-on cell. Such cells would be filled with a liquid or semi-liquid electrolyte (e.g., Kihira et al, U.S. Pat. No. 4,806,849) or a spongy medium impregnated with a liquid electrolyte (e.g., Kondou et al, U.S. Pat. No. 5,221,893) with remote electrodes immersed in the electrolyte or in intimate contact with the electrolyte-impregnated sponge. These cells required an accessible, flat, smooth, and horizontal area. The set-up was considered to be time consuming and had to be performed for each measurement. Corrosion was detected only directly under the cell and use of the cell actually caused artifactual damage to the coating in many instances because of exposure to the electrolyte during measurement.

Davis et al, U.S. Pat. No. 5,859,537, developed a painted electrode sensor which eliminates many of the problems discussed above. The actual structure is being inspected without exposure to an extrinsic electrolyte. Measurements are possible under most natural or accelerated conditions and material and coating degradation are detectable from the very early stages. However, the Davis et al, sensor requires an electrode to be permanently painted onto the structure and is time-consuming for all the fabrication steps to be completed. It is not suitable for structures in which appearance or aerodynamics precludes an attached sensor. The sensor can induce artifactual damage in a small class of materials, primarily porous coatings.

Further prior art approaches include galvanic sensors that combine two different materials and sense electric current flows between the two.

In another prior art application linear polarization resistance (LPR) has been used. In the LPR technique, a potential (typically of the order of 10-20 mV) is applied to a sensor element and the resulting ("linear") current response is measured. This small potential perturbation is usually applied step-wise, starting below the free corrosion potential and terminating above the free corrosion potential. The polarization resistance is the ratio of the applied potential and the resulting current response. This "resistance" is inversely related to the uniform corrosion rate.

Douglas (U.S. Pat. No. 6,843,135) describes an application of using magnetic detectors to monitor corrosion inside of enclosed containers using sacrificial coupons. This approach makes use of spring-loaded coupons that are designed to fail when a specified level of corrosion occurs. A permanent magnet located on the corrosion coupon is used to transmit the failure of the coupon outside of the container. While this approach has potential to provide a contact less monitoring technique, a more continuous monitoring that would indicate a developing problem is much more desirable.

Magnetic Sensors. One sensor field of high potential is more modern magnetic sensors. These include, among others, eddy current, Hall effect, and giant magneto resistor sensors These detect changes, or disturbances, in magnetic fields that have been created or modified, and from them derive information on properties such as direction, presence, rotation, angle, or electrical currents. The output signal of these sensors requires some signal processing for translation into the desired parameter. Although magnetic detectors have been considered somewhat more difficult to use, they potentially provide more accurate and reliable data—without physical contact.

In eddy current inspection, the eddy currents are generated in the test material due to mutual induction. The test probe is basically a coil of wire through which alternating current is passed. When alternating current is passed through the coil, a magnetic field is generated in and around the coil. When the probe is brought in close proximity to a conductive material, such as aluminum, the probe's changing magnetic field generates current flow in the material. The induced current flows in closed loops in planes perpendicular to the magnetic flux. They are named eddy currents because they are thought to resemble the eddy currents that can be seen swirling in streams.

Eddy currents produce their own magnetic fields that interact with the primary magnetic field of the coil. By measuring changes in the resistance and inductive reactance of the coil, information can be gathered about the test material. This information includes the electrical conductivity and magnetic permeability of the material, the amount of material cutting through the coils magnetic field, and the condition of the material (i.e. whether it contains cracks or other defects.) The distance that the coil is from the conductive material is called liftoff, and this distance affects the mutual-inductance of the circuits. Liftoff can be used to make measurements of the thickness of nonconductive coatings, such as paint, that hold the probe a certain distance from the surface of the conductive material.

There are several sensors that use the Lorentz force, or Hall effect, on charge carriers in a semiconductor. The Lorentz force equation describes the force $F_L$ experienced by a charged particle with charge q moving with velocity v in a magnetic field B:

$$F_L = q(v \times B)$$

Since $F_L$, v, and B are vector quantities, they have both magnitude and direction. The Lorentz force is proportional to the cross product between the vectors representing velocity and magnetic field; it is therefore perpendicular to both of them and, for a positively charged carrier, has the direction of advance of a right-handed screw rotated from the direction of v toward the direction of B. The acceleration caused by the Lorentz force is always perpendicular to the velocity of the charged particle; therefore, in the absence of any other forces, a charge carrier follows a curved path in a magnetic field.

Hall Effect Sensors. The Hall effect is a consequence of the Lorentz force in semiconductor materials. When a voltage is applied from one end of a slab of semiconductor material to the other, charge carriers begin to flow. If at the same time a magnetic field is applied perpendicular to the slab, the current carriers are deflected to the side by the Lorentz force. Charge builds up along the side until the resulting electrical field produces a force on the charged particle sufficient to counteract the Lorentz force. This voltage across the slab perpendicular to the applied voltage is called the Hall voltage.

Magnetoresistors. The simplest Lorentz force devices are magneto resistors that use semiconductors such as InSb and InAs with high room-temperature carrier mobility. If a voltage is applied along the length of a thin slab of semiconductor material, a current will flow and a resistance can be measured. When a magnetic field is applied perpendicular to the slab, the Lorentz force will deflect the charge carriers. If the width of the slab is greater than the length, the charge carriers will cross the slab without a significant number of them collecting along the sides. The effect of the magnetic field is to increase the length of their path and, thus, the resistance. An increase in resistance of several hundred percent is possible in large fields. To produce sensors with hundreds to thousands of ohms of resistance, long, narrow semiconductor stripes a few micrometers wide are produced using photolithography. The required length-to-width ratio is accomplished by forming periodic low-resistance metal shorting bars across the traces. Each shorting bar produces an equipotential across the semiconductor stripe. The result is, in effect, a number of small semiconductor elements with the proper length-to-width ratio connected in series.

Magnetoresistors formed from InSb are relatively insensitive in low fields; in high fields, however, they exhibit a resistance that changes approximately as the square of the field. They are sensitive only to that component of the magnetic field perpendicular to the slab and not to whether the field is positive or negative. Their large temperature coefficients of resistivity are caused by the change in mobility of the charge carriers with temperature. The sensors are made with either single resistors or pairs of spaced resistors. The latter are used to measure field gradients and are sometimes combined with external resistors to form a Wheatstone bridge. A permanent magnet is often incorporated in the field gradient sensor to bias the magnetoresistors up to a more sensitive part of their characteristic curve.

Integrated Hall sensors. Hall devices are often combined with semiconductor elements to create integrated sensors. Adding comparators and output devices to a Hall element, for example, yields unipolar and bipolar digital switches. Adding an amplifier increases the relatively low voltage signals from a Hall device to produce ratiometric linear Hall sensors with an output centered on one-half the supply voltage. Power usage can even be reduced to extremely low levels by using a low duty cycle.

Giant Magnetoresistive (GMR) Devices. Large magnetic field dependent changes in resistance are possible in thin film ferromagnet/nonmagnetic metallic multilayers. Changes in resistance with magnetic field of up to 70% have been seen. Compared to the small percent change in resistance observed in anisotropic magnetoresistance, this phenomenon was truly giant magnetoresistance.

The resistance of two thin ferromagnetic layers separated by a thin nonmagnetic conducting layer can be altered by changing the moments of the ferromagnetic layers from parallel to antiparallel, or parallel but in the opposite direction.

GMR materials for magnetic field sensors are sometimes used in Wheatstone bridge configurations, although simple GMR resistors and GMR half bridges can also be fabricated. A sensitive bridge can be made from four photolithographically patterned GMR resistors, two of which are active elements. These resistors can be as narrow as 2 μm, allowing a serpentine 10 k resistor to be patterned in an area as small as 100 μm$^2$. The vary narrow width also makes the resistors sensitive only to the magnetic field component along their long dimension. Small magnetic shields are plated over two of the four equal resistors in a Wheatstone bridge, protecting them from the applied field and allowing them to act as reference resistors. Since they are fabricated from the same material, they have the same temperature coefficient as the active resistors. The two remaining GMR resistors are both exposed to the external field. The bridge output is therefore twice the output from a bridge with only one active resistor. The bridge output for a 10% change in these resistors is ~5% of the voltage applied to the bridge.

Smart sensors with sensing elements and associated electronics such as amplification and signal conditioning on the same die are the latest trend. GMR materials are sputtered onto wafers and can therefore be directly integrated with semiconductor processes. The small sensing elements fit well with the other semiconductor structures and are applied after most of the semiconductor fabrication operations are complete. Because of the topography introduced by the many layers of polysilicon, metal, and oxides over the transistors, areas must be reserved with no underlying transistors or connections. These areas will have the GMR resistors. The GMR materials are actually deposited over the entire wafer, but the etched sensor elements remain only on these reserved, smooth areas on the wafers.

Among the functions built into an integrated sensor are regulated voltage or current supplies to the sensor elements; threshold detection to provide a switched output when a preset field is reached; amplifiers; logic functions, including divide-by-2 circuits; and various options for outputs. With these elements, a 2-wire sensor can be designed that has two current levels—low when the field is below a threshold and high when the field is above the threshold.

Onboard sensor electronics can increase signal levels to significant voltages with the least pickup of interference. It is always best to amplify low-level signals close to where they are generated. Converting analog signals to digital (switched) outputs within the sensor is another way to minimize electronic noise. The use of comparators and digital outputs makes the nonlinearity in the output of sandwich GMR materials of less concern. Even the hysteresis in such materials can be useful, since some hysteresis is usually built into comparators to avoid multiple triggering of the output due to noise.

GMR materials have been successfully integrated with both BiCMOS and bipolar semiconductor underlayers. The wafers are processed with all but the final layer of connections complete. GMR material is deposited on the surface and patterned. The next step is the application of a passivation layer through which windows are cut to permit contact to both the upper metal layer in the semiconductor wafer and to the GMR resistors. The final layer of metal is then deposited and patterned to interconnect the GMR sensor elements and to connect them to the semiconductor underlayers. This layer also forms the pads to which wires will be bonded during packaging. A final passivation layer is deposited, magnetic shields and flux concentrators are plated and patterned, and windows are etched through to the pads.

The potential accuracy and reliability of magnetic sensors, coupled with their contact-less aspect, make them potential candidates for environmental damage sensors. Although it is known that the magnetic activity of a corroding sample can be used for non-destructive and real-time quantification of electrochemical corrosion activity, defined practical systems for making use of this characteristic have not been disclosed. What is needed are new magnetic sensor systems that take advantage of these characteristics in the unique application of remote, unmanned long term environmental monitoring of structures.

What is needed therefore is an apparatus and method for continuously measuring environmental degradation in the environment of a structure that provides the accuracy and reliability of magnetic measurement technology. Providing this is an aspect of the instant invention.

SUMMARY

The needs discussed are addressed by the instant invention.

One aspect of the invention is a sensor apparatus for measuring environmental degradation in the environment of a structure including at least: a first magnetic field sensor element with associated electronics mounted in a fixed position in a sensor housing, the sensor housing mounted in close proximity to the structure; a first sacrificial material coupon mounted in a fixed position in the immediate vicinity of the magnetic field sensor element, the first sacrificial material coupon being chosen to represent the material of the structure and being mounted so as to be exposed to the environment of the structure; wherein the associated electronics is effective to capture and record magnetic field strength or magnetic fluxes over time as measured by the first magnetic field sensor element.

Another aspect of the invention is a sensor apparatus for measuring environmental degradation in the environment of a structure including at least: a first magnetic field sensor element with associated electronics mounted in a fixed position in a sensor housing, the sensor housing mounted in close proximity to the structure; a first sacrificial material coupon mounted in a fixed position in the immediate vicinity of the magnetic field sensor element, the first sacrificial material coupon being chosen to represent the material of the structure and being mounted so as to be exposed to the environment of the structure; a second sacrificial material coupon with associated electronics mounted in a fixed position in the immediate vicinity of a second magnetic field sensor element, the second material coupon mounted so as to not be exposed to the environment of the structure; wherein the second sacrificial material coupon is of the same material of the first sacrificial material coupon; wherein the associated electronics is effective to capture and record magnetic field strength or magnetic flux differences between said first and second magnetic sensor elements over time.

Another aspect of the invention is a sensor apparatus for measuring environmental degradation in the environment of a structure including at least: a first magnetic field sensor element with associated electronics mounted in a fixed position in a sensor housing; a first sacrificial material coupon mounted in a fixed position in the immediate vicinity of the magnetic field sensor element, the first sacrificial material coupon being chosen to represent the material of the structure and being mounted so as to be exposed to the environment of the structure; wherein the associated electronics is effective to capture and record magnetic field strength or magnetic fluxes over time as measured by the first magnetic field sensor element further including rigidly fixing the first sacrificial material coupon directly to the structure.

Another aspect of the invention is a method for measuring environmental degradation in the environment of a structure comprising the steps of: mounting a first magnetic field sensor element with associated electronics in a fixed position in a sensor housing, the sensor housing mounted in close proximity to the structure; mounting a first sacrificial material coupon in a fixed position in the immediate vicinity of the magnetic field sensor element, wherein the first sacrificial material coupon is chosen to represent the material of the structure and is mounted so as to be exposed to the environment of the structure; and capturing and recording magnetic field strength or magnetic fluxes over time as measured by the first magnetic field sensor element and using those recordings to measure the environmental degradation in the environment of the structure.

Another aspect of the invention is a method for measuring environmental degradation in the environment of a structure comprising the steps of: mounting a first magnetic field sensor element with associated electronics in a fixed position in a sensor housing, the sensor housing mounted in close proximity to the structure; mounting a first sacrificial material coupon in a fixed position in the immediate vicinity of the magnetic field sensor element, wherein the first sacrificial material coupon is chosen to represent the material of the structure and is mounted so as to be exposed to the environment of the structure; mounting a second sacrificial material coupon in a fixed position in the immediate vicinity of a second magnetic field sensor element with associated electronics, the second material coupon mounted so as to not be exposed to the environment of the structure; wherein the second sacrificial material coupon is of the same material of the first sacrificial material coupon; and recording differences in magnetic field strengths detected between the first and the second magnetic field sensor elements over time, and using those recordings to measure the environmental degradation in the environment of the structure.

Another aspect of the invention is a method for measuring environmental degradation in the environment of a structure comprising the steps of: mounting a first magnetic field sensor element with associated electronics in a fixed position in a sensor housing, the sensor housing mounted in close proximity to the structure; mounting a first sacrificial material coupon in a fixed position in the immediate vicinity of the magnetic field sensor element, wherein the first sacrificial material coupon is chosen to represent the material of the structure and is mounted so as to be exposed to the environment of the structure; further including rigidly fixing the first sacrificial material coupon directly to the structure and; capturing and recording magnetic field strength or magnetic fluxes over time as measured by the first magnetic field sensor element and using those recordings to measure the environmental degradation in the environment of the structure.

To insure that a clear and complete explanation is given to enable a person of ordinary skill in the art to practice the invention some specific examples will be given involving applying the instant invention to particular structures and with particular magnetic field sensors. It should be understood though that the inventive concept could apply to other structures, using other magnetic field sensors and the specific example is not intended to limit the inventive concept to the example application.

DETAILED DESCRIPTION

Figure 1:
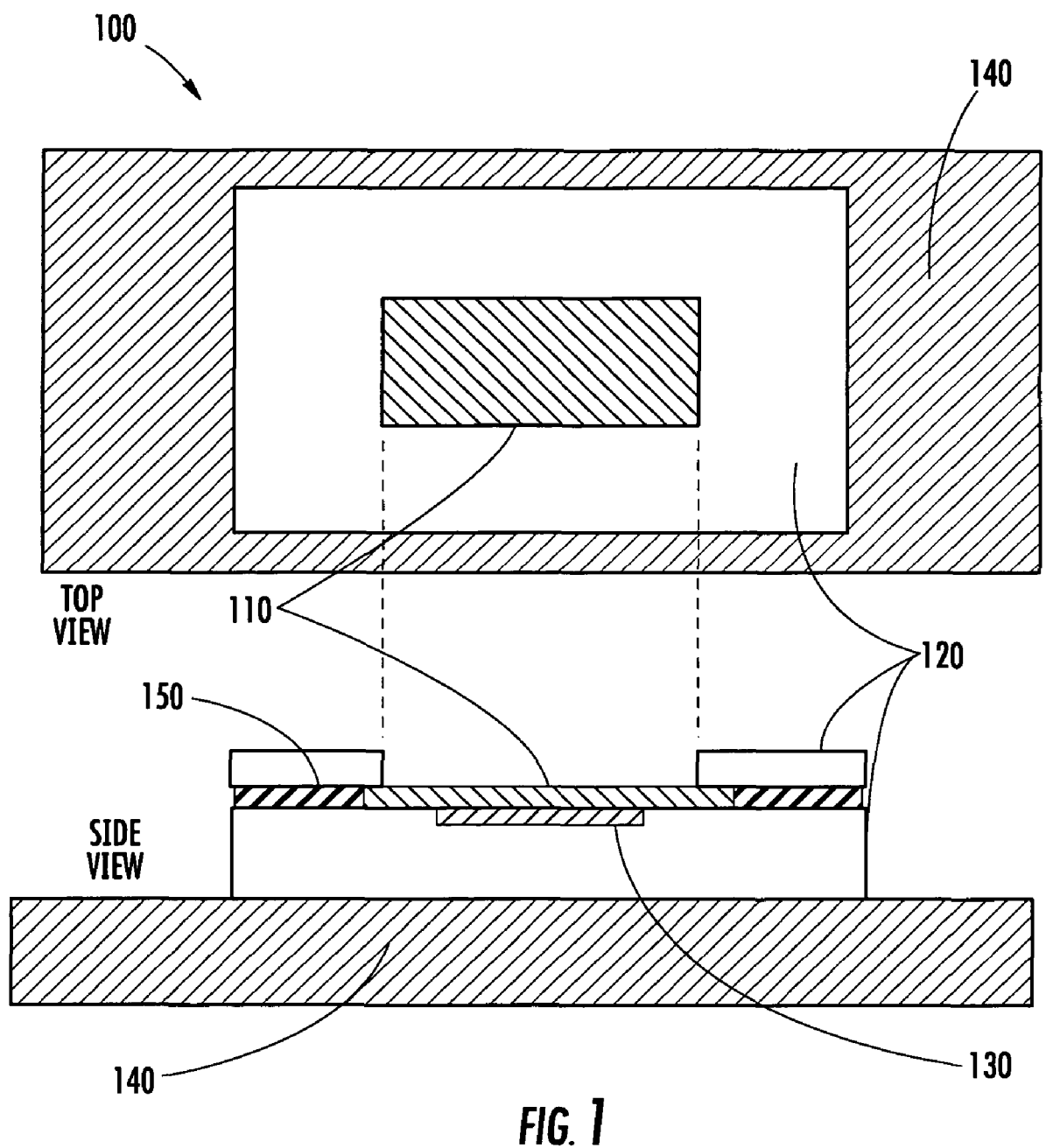
FIG. 1 is a side and top view of one aspect of the invention.

FIG. 1 represented generally by the numeral 100 illustrates an aspect of the instant invention. A magnetic sensor element 130 is mounted in a fixed position in a sensor housing 120. The sensor housing 120 is mounted on or in close proximity to the structure 140 that is being monitored. The sensor housing could be made of any number of non-magnetic materials, such as aluminum, or a plastic material. Mounted in close proximity or in direct contact to sensor element 130 is a sacrificial material coupon 110. Sacrificial material coupon 110 is chosen to match the material of structure 140. As shown in FIG. 1 a significant portion of sacrificial material coupon 110 is exposed to the environment surrounding structure 140. Element 150 is a spacer or gasket to aid in mounting sacrificial material coupon 110 and is not critical to the instant invention. It should be noted that FIG. 1 indicates a sensor housing 120 as being made up of separate parts but could also be an integral single piece surrounding sensor housing 120 and sacrificial material coupon 110. Not shown in the FIG. 1 is the electronics associated with sensor element 130 that would capture and record magnetic field strength or magnetic fluxes over time. The data collected could be stored integrally in memory in sensor housing 120, or transmitted by wiring or wirelessly to remote environmental monitoring equipment.

Magnetic sensor 130 could for example be a AD22151G linear output magnetic field transducer (Hall Effect) manufactured by Analog Devices of Norwood, Mass. Alternately a giant magnetoresistance detector such as model AAH-004-00 magnetometer, manufactured by NVE Corporation of Eden Prairie, Minn. These sensors, as well as select eddy current sensors are suited to this application.

Figure 2:
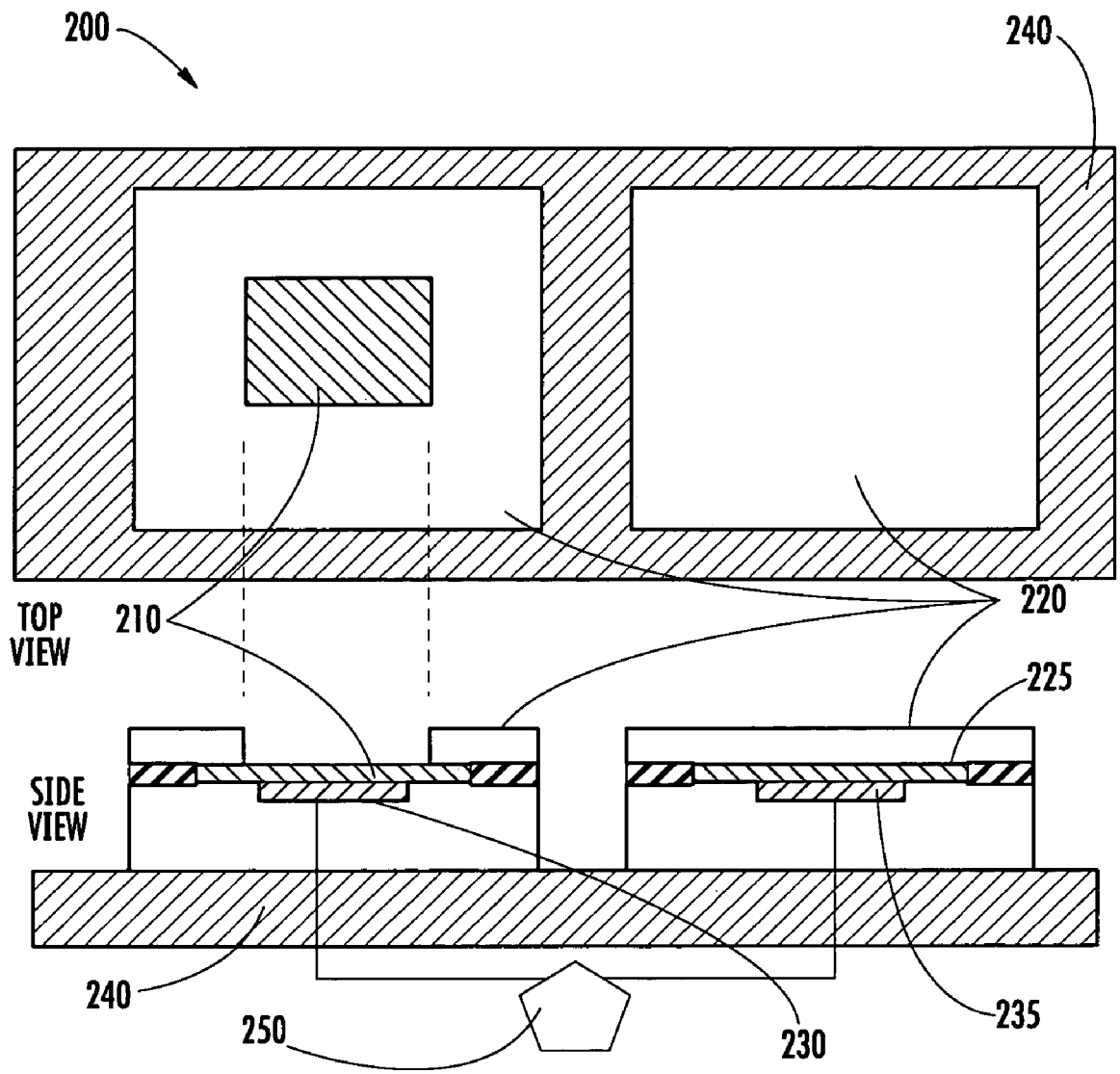
FIG. 2 is a side and top view of one aspect of the invention.

FIG. 2, represented generally by the numeral 200, illustrates a further application of the instant invention. A first magnetic sensor element 230 is mounted in a fixed position in a sensor housing 220. The sensor housing 220 is mounted on or in close proximity to the structure 240 that is being monitored. The sensor housing could be made of any number of non-magnetic materials, such as aluminum, or a plastic material. Mounted in close proximity or in direct contact to sensor element 230 is a sacrificial material coupon 210. Sacrificial material coupon 210 is chosen to match the material of structure 240. As shown in FIG. 2 a significant portion of sacrificial material coupon 210 is exposed to the environment surrounding structure 240. A second magnetic sensor element 235 is mounted in a fixed position in a sensor housing 220. A second sacrificial material coupon 225 is mounted in close proximity or in contact with magnetic sensor element 235. Sacrificial material coupon 225 is sealed from exposure to the environment by being sealed inside sensor housing 220. In practice magnetic sensor elements 230 and 235 would be identical in nature, as would the material of sacrificial material coupons 210 and 225. Magnetic sensor elements 210 and 235 are in communication, either wired or wirelessly with a differential measurement system 250 to measure and record the differences in magnetic field or magnetic flux measurements. This aspect of the invention allows environmental degradation to be measured as the difference between two relatively identical sacrificial material coupons, one being exposed to the environment and the other not exposed. It should be noted that although the two sensor housings are shown as separate, in practice this could be an integral sensor housing.

Figure 3:
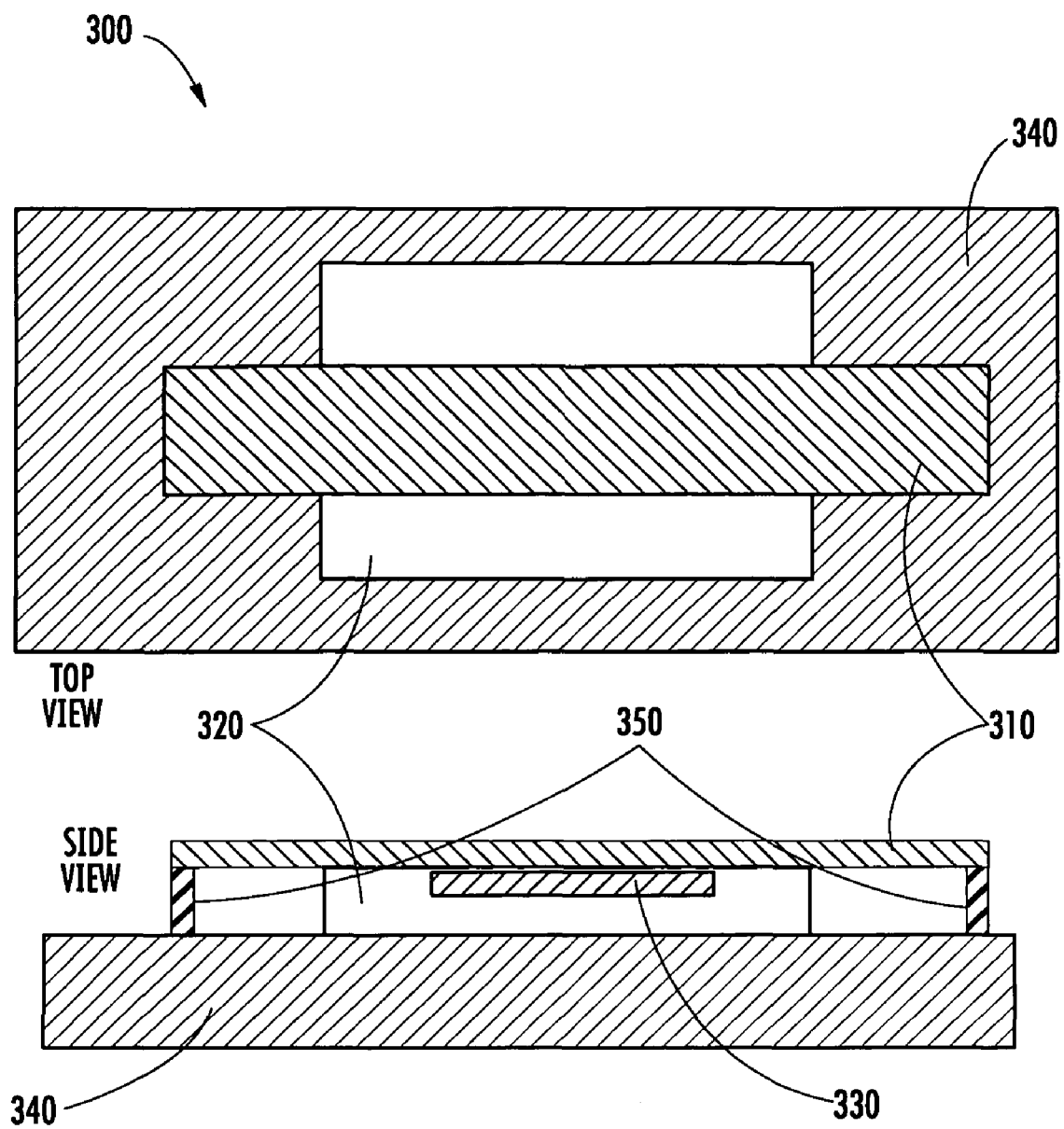
FIG. 3 is a side and top view of one aspect of the invention.

FIG. 3, represented generally by the numeral 300, represents another embodiment of the instant invention. In some applications it is desired to measure the environmental degradation of a sacrificial material coupon experiencing the same stress history as the underlying structure. In this embodiment the sensor housing 320, containing the fixed magnetic sensor element 330 is mounted onto structure 340. Sacrificial material coupon 310 is placed in close proximity to magnetic sensor element 330 but in addition is rigidly fixed to structure 340 with mounting elements 350. Other means, such as a load frame (not shown) could be used couple the sacrificial material coupon to the structure. Not shown in FIG. 3 is the electronics associated with sensor element 330 that would capture and record magnetic field strength or magnetic fluxes over time. The data collected could be stored integrally in memory in sensor housing 320, or transmitted by wiring or wirelessly to remote environmental monitoring equipment.

Processing of the data from these various aspects of the invention is used to monitor corrosion. A number of possibilities exist. Field strength as measured by the sensor is proportional to current, which is proportional to actual damage. The corrosion magnetic field contains spatial and temporal information that correlate with the distribution, magnitude, and time course of currents associated with electrochemical corrosion. In conjunction with appropriate calibration experiments, the magnetic activity of a corroding sample can be used for non-destructive and real-time quantification of electrochemical corrosion activity of non-ferromagnetic metals.

In practice the practitioner would continuously integrate the measured field to thus have a measure of corrosion damage from time zero to current time. In addition the collected data allows the accumulation of a time history of the amount and rate of corrosion damage.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

The invention claimed is:

1. A sensor apparatus for measuring environmental degradation in the environment of a structure comprising:
    a. a first magnetic field sensor element with associated electronics mounted in a fixed position in a sensor housing, said sensor housing mounted in close proximity to said structure;
    b. a first sacrificial material coupon mounted in a fixed position in the immediate vicinity of said magnetic field sensor element, said first sacrificial material coupon being chosen to represent the material of said structure and being mounted so as to be exposed to said environment of said structure;
    c. wherein said associated electronics is effective to capture and record magnetic field strength over time or magnetic fluxes over time as measured by said first magnetic field sensor element.

2. The sensor apparatus for measuring environmental degradation in the environment of a structure of claim 1 further comprising:
    a. a second sacrificial material coupon with associated electronics mounted in a fixed position in the immediate vicinity of a second magnetic field sensor element, said second material coupon mounted so as to not be exposed to the environment of said structure; wherein said second sacrificial material coupon is of the same material of said first sacrificial material coupon; and
    b. wherein said associated electronics is effective to capture and record magnetic field strength or magnetic flux differences between said first and second magnetic sensor elements over time.

3. The sensor apparatus of claim 1 wherein said first magnetic field sensor element is selected from the group consisting of: an eddy current sensor, a Hall effect sensor, and a giant magneto resistance sensor.

4. The sensor apparatus of claim 2 wherein said first magnetic field sensor element and said second magnetic field sensor element is selected from the group consisting of: an eddy current sensor, a Hall effect sensor, and a giant magneto resistance sensor.

5. The sensor apparatus of claim 3 further comprising rigidly fixing said first sacrificial material coupon directly to said structure.

6. A method for measuring environmental degradation in the environment of a structure comprising the steps of:
    a. mounting a first magnetic field sensor element with associated electronics in a fixed position in a sensor housing, said sensor housing mounted in close proximity to said structure;
    b. mounting a first sacrificial material coupon in a fixed position in the immediate vicinity of said magnetic field sensor element, wherein said first sacrificial material coupon is chosen to represent the material of said structure and is mounted so as to be exposed to said environment of said structure; and
    c. capturing and recording magnetic field strength over time or magnetic fluxes over time as measured by said first magnetic field sensor element and using those recordings to measure the environmental degradation in the environment of said structure.

7. The method of claim 6 further comprising the steps of:
    a. mounting a second sacrificial material coupon in a fixed position in the immediate vicinity of a second magnetic field sensor element with associated electronics, said second material coupon mounted so as to not be exposed to the environment of said structure; wherein said second sacrificial material coupon is of the same material of said first sacrificial material coupon; and
    b. recording differences in magnetic field strengths detected between said first and said second magnetic field sensor elements over time, and using those recordings to measure the environmental degradation in the environment of said structure.

8. The method of claim 6 further comprising the step of rigidly fixing said first sacrificial material coupon directly to said structure.

\* \* \* \* \*